US012678417B2

(12) United States Patent
Jackson et al.

(10) Patent No.: US 12,678,417 B2
(45) Date of Patent: Jul. 14, 2026

(54) PET FOOD COMPOSITIONS

(71) Applicant: Hill's Pet Nutrition, Inc., Topeka, KS (US)

(72) Inventors: Matthew Jackson, Topeka, KS (US); Dennis Jewell, Lawrence, KS (US)

(73) Assignee: Hill's Pet Nutrition, Inc., Overland Park, KS (US)

( * ) Notice: Subject to any disclaimer, the term of this patent is extended or adjusted under 35 U.S.C. 154(b) by 416 days.

(21) Appl. No.: 18/268,797

(22) PCT Filed: Dec. 19, 2021

(86) PCT No.: PCT/US2021/064253
§ 371 (c)(1),
(2) Date: Jun. 21, 2023

(87) PCT Pub. No.: WO2022/140210
PCT Pub. Date: Jun. 30, 2022

(65) Prior Publication Data
US 2024/0058290 A1 Feb. 22, 2024

Related U.S. Application Data

(60) Provisional application No. 63/129,146, filed on Dec. 22, 2020.

(51) Int. Cl.
*A61K 31/198* (2006.01)
*A23K 10/30* (2016.01)
(Continued)

(52) U.S. Cl.
CPC ............ *A61K 31/198* (2013.01); *A23K 10/30* (2016.05); *A23K 20/142* (2016.05);
(Continued)

(58) Field of Classification Search
None
See application file for complete search history.

(56) References Cited

U.S. PATENT DOCUMENTS

2019/0008186 A1 1/2019 Jackson et al.
2019/0240180 A1* 8/2019 Li ......................... A61K 31/202
(Continued)

FOREIGN PATENT DOCUMENTS

CN 1251021 A 4/2000
CN 101951786 A 1/2011
(Continued)

OTHER PUBLICATIONS

Ephraim et al. (Effect of added dietary betaine and soluble fibers and fecal microbiome in dogs with early renal disease), Metabolites, 10, 0370, Sep. 2020.*
(Continued)

*Primary Examiner* — Isis A Ghali

(57) ABSTRACT
Described herein are pet food compositions comprising an amino acid component comprising: lysine; betaine; and glutamic acid and/or a salt thereof present in an amount of about 7 wt. % or more, based on the total weight of the pet food composition; and about 3.3 wt. % or more, of a fatty acid component comprising a fatty acid having an aliphatic tail of 6 to 12 carbons and/or an omega-3 fatty acid, based on the total weight of the pet food composition.

10 Claims, 5 Drawing Sheets

(51) Int. Cl.

| | | |
|---|---|---|
| *A23K 20/142* | (2016.01) | |
| *A23K 20/158* | (2016.01) | |
| *A23K 50/40* | (2016.01) | |
| *A61K 31/205* | (2006.01) | |
| *A61K 36/21* | (2006.01) | |
| *A61K 36/45* | (2006.01) | |
| *A61K 36/55* | (2006.01) | |
| *A61K 36/752* | (2006.01) | |
| *A61P 1/14* | (2006.01) | |

(52) U.S. Cl.
CPC ............ *A23K 20/158* (2016.05); *A23K 50/40* (2016.05); *A61K 31/205* (2013.01); *A61K 36/21* (2013.01); *A61K 36/45* (2013.01); *A61K 36/55* (2013.01); *A61K 36/752* (2013.01); *A61P 1/14* (2018.01)

(56) References Cited

U.S. PATENT DOCUMENTS

| | | |
|---|---|---|
| 2019/0350226 A1 | 11/2019 | Gebresalassie et al. |
| 2020/0296996 A1 | 9/2020 | Jackson et al. |

FOREIGN PATENT DOCUMENTS

| | | |
|---|---|---|
| CN | 104619195 A | 5/2015 |
| CN | 105211641 A | 1/2016 |
| CN | 111511219 A | 8/2020 |
| JP | 2019-500047 A | 1/2019 |
| JP | 2020-503034 A | 1/2020 |
| WO | WO-2009086275 A1 * | 7/2009 ............. A23K 40/20 |
| WO | 2017/117091 A1 | 7/2017 |
| WO | 2018/125693 A1 | 7/2018 |

OTHER PUBLICATIONS

Brindha et al. "Cost effective utilization of poultry and cruciferous vegetable waste as a raw material to develop a shelf-stable pet food", Journal of Animal Research and Nutrition, vol. 2, No. 1:7 (Year: 2017).*

European Food Safety Authority ("Scientific opinion on safety and efficacy of the use of amino acids (chemical group 34) when used as flavouring for all animal feed (FEEDAP)", EFSA Journal 12(5): 3670 (Year: 2014).*

Anonymous, 2018, "Technical Data Sheet Captex 355", https://www.ulprospector.com/es/na/PersonalCare/Detail/601/24596/Captex-355, retrieved Apr. 5, 2022, pp. 1-1.

Filipcev et al., 2018, "Betaine in Cereal Grains and Grain-Based Products", Foods, 7(4):49, pp. 1-11.

International Search Report and the Written Opinion of the International Searching Authority issued in International Application PCT/US2021/064253 mailed Apr. 13, 2022.

Kathrani et al., 2018, "Alterations in serum amino acid concentrations in dogs with protein-losing enteropathy", Journal of Veterinary Internal Medicine, 32:1026-1032.

Schmitz et al., 2019, "Diagnostic features, treatment, and outcome of dogs with inflammatory protein-losing enteropathy," Journal of Veterinary Internal Medicine, 33:2005-2013.

Seong et al., 2015, "Characterization of Chicken By-products by Mean of Proximate and Nutritional Compositions", Korean Society for Food Science of Animal Resources, https://www.ncbi.nlm.nih.gov/pmc/articles/PMC4682518/pdf/kosfa-35-179.pdf, retrieved Apr. 5, 2022, Korean J. Food Sci. An., 35(2):179-188.

* cited by examiner

PET FOOD COMPOSITIONS

CROSS-REFERENCE TO RELATED APPLICATIONS

This application is a U.S. National Stage application of PCT/US2021/064253, filed Dec. 19, 2021, which claims the benefit of priority from U.S. Provisional Application No. 63/129,146, filed Dec. 22, 2020, the contents of which are hereby incorporated herein by reference in their entireties.

BACKGROUND

Inflammatory bowel disease (IBD) can be an existential threat to animals (Schmitz et al., *J Vet Intern Med.,* 2019, September; 33(5):2005-2013). Protein losing enteropathy associated with IBD results in the loss of endogenous hemostatic albumin and immunoglobins through a degraded gut barrier (Allenspach et al., *J Vet Intern Med.,* 2018, May; 32(3):1026-1032). Treatment options for such loss are limited. Dietary solutions which increase circulating protein status have potential clinical value for such animals.

Dogs suffering from IBD may exhibit reduced appetite and thus struggle to achieve adequate protein and energy intake. For many instances of dogs with chronic gastroenteritis from food allergies or IBD, therapeutic foods that are relatively low in protein are often recommended and employed because they are well tolerated and contain protein at levels which do not lead to gastrointestinal distress, such as colonic putrefaction, or dysbiosis. However, being able to provide for food compositions having higher levels of protein may be beneficial. A formulation having higher level of protein may allow for adequate protein intake even in the situation of less-than recommended consumption of a food.

It would therefore be desirable to provide a pet food composition which may beneficially affect animals suffering from IBD, such as by increasing the circulating protein of the animal, increasing biomarkers associated with health, and/or modifying the gut microbiome.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Applicants have discovered that utilization of certain ingredients within a pet food composition provides for effective health benefits. In one aspect, the health benefit may be to increase the lean mass of the animal. In another aspect, the health benefit may be to increase the lean mass of an obese animal. In another aspect, the health benefit may be to increase the lean mass of a dog. Thus, in one aspect, the invention is a pet food composition comprising soluble fiber and certain mass ratios of linolenic acid to total 18 carbon polyunsaturated fatty acids.

In at least one embodiment, the present invention is directed to a pet food composition comprising lysine, betaine, and glutamic acid present in a total amount of about 7% or more, based on the weight of the pet food composition; and C8 fatty acid, C10 fatty acid, and omega-3 C18 fatty acid present in a total amount of about 3.3% or more, based on the weight of the pet food composition. In certain embodiments, the weight ratio of lysine, betaine, and glutamic acid is from about 5.4:1:7.6 to about 6.5:1:9.1. In certain embodiments, the weight ratio of lysine, betaine, and glutamic acid is about 5.4:1:7.6. In certain embodiments, the weight of lysine is from about 2% to about 3.3%; betaine is from about 0.4% to about 0.6%; and glutamic acid is from about 3% to about 4.6%, based on the weight of the pet food composition. In certain embodiments, the weight of lysine is about 2.7%; betaine is about 0.5%; and glutamic acid is about 3.8%, based on the weight of the pet food composition. In certain embodiments, the weight ratio of C8 fatty acid, C10 fatty acid, and omega-3 C18 fatty acid is from about 2.21:1.86:1 to about 2.65:2.23:1. In certain embodiments, the weight ratio of C8 fatty acid, C10 fatty acid, and omega-3 C18 fatty acid is about 2.21:1.86:1. In certain embodiments, the weight of C8 fatty acid is from about 1.15% to about 1.73%; C10 fatty acid is from about 0.97% to about 1.45%; and omega-3 C18 fatty acid is from about 0.52% to about 0.78%, based on the weight of the pet food composition. In certain embodiments, the weight of C8 fatty acid is about 1.44%; C10 fatty acid is about 1.21%; and omega-3 C18 fatty acid is about 0.65%, based on the weight of the pet food composition. In certain embodiments, the composition further comprises flax, citrus pulp, beet pulp, and cranberry pomace. In certain embodiments, the flax, citrus pulp, beet pulp, and cranberry pomace is present in a total amount of about 6% or more, based on the weight of the pet food composition. In certain embodiments, the weight ratio of flax, citrus pulp, beet pulp, and cranberry pomace is from about 2:1.5:1.5:1 to about 2.4:1.8:1.8:1. In certain embodiments, the weight ratio of flax, citrus pulp, beet pulp, and cranberry pomace is about 2:1.5:1.5:1. In certain embodiments, the weight of flax is from about 1.6% to about 2.4%; citrus pulp is from about 1.2% to about 1.8%; beet pulp is from about 1.2% to about 1.8%, and cranberry pomace is from about 0.8% to about 1.2%, based on the weight of the pet food composition. In certain embodiments, the weight of flax is about 2%; citrus pulp is about 1.5%; beet pulp is about 1.5%, and cranberry pomace is about 1.0%, based on the weight of the pet food composition.

In further embodiments, the invention is directed to a method for treating, preventing, or ameliorating gut microbiome putrefaction in a companion animal, comprising feeding an effective amount of the composition according to any one of the embodiments described herein to a companion animal in need thereof. In certain embodiments, the companion animal is a dog.

In other embodiments, the invention is directed to a pet food composition for mitigating gut microbiome putrefaction, comprising lysine, betaine, and glutamic acid present in a total amount of about 7% or more, based on the weight of the pet food composition; C8 fatty acid, C10 fatty acid, and omega-3 C18 fatty acid present in a total amount of about 3.3% or more, based on the weight of the pet food composition; and flax, citrus pulp, beet pulp, and cranberry pomace present in a total amount of about 6% or more, based on the weight of the pet food composition. In certain embodiments, the weight ratio of lysine, betaine, and glutamic acid is from about 5.4:1:7.6 to about 6.5:1:9.1. In certain embodiments, the weight ratio of lysine, betaine, and glutamic acid is about 5.4:1:7.6. In certain embodiments, the weight of lysine is from about 2% to about 3.3%; betaine is from about 0.4% to about 0.6%; and glutamic acid is from about 3% to about 4.6%, based on the weight of the pet food composition. In certain embodiments, the weight of lysine is about 2.7%; betaine is about 0.5%; and glutamic acid is about 3.8%, based on the weight of the pet food composition. In certain embodiments, the weight ratio of C8 fatty acid, C10 fatty acid, and omega-3 C18 fatty acid is from about 2.21:1.86:1 to about 2.65:2.23:1. In certain embodiments, the weight ratio of C8 fatty acid, C10 fatty acid, and omega-3 C18 fatty acid is about 2.21:1.86:1. In certain embodiments, the weight of C8 fatty acid is from about 1.15% to about 1.73%; C10 fatty acid is from about 0.97% to about 1.45%; and omega-3 C18 fatty acid is from about 0.52% to about 0.78%, based on the weight of the pet food composition. In certain embodiments, the weight of C8 fatty acid is about 1.44%; C10 fatty acid is about 1.21%; and omega-3 C18 fatty acid is about 0.65%, based on the weight of the pet food composition.

In further embodiments, the invention is directed to a method for mitigating gut microbiome putrefaction in a companion animal, comprising feeding an effective amount of the composition according to any one of the embodiments described herein to a companion animal in need thereof. In certain embodiments, the companion animal is a dog.

Further areas of applicability of the present invention will become apparent from the detailed description provided hereinafter. It should be understood that the detailed description and specific examples, while indicating the typical embodiments of the invention, are intended for purposes of illustration only and are not intended to limit the scope of the invention.

BRIEF DESCRIPTION OF THE DRAWINGS

The detailed description of the invention will be better understood when read in conjunction with the appended drawings. It should be understood, however, that the invention is not limited to the precise arrangements and instrumentalities of the embodiments shown in the drawings.

FIG. 2b depicts a chart showing the result comparison on stool pH from dogs fed pet food compositions. FIG. 2c depicts a chart showing the result comparison on stool proteolytic/putrefactive branched short chain fatty acids (bSCFA) bscfa Ile, bscfa Leu, and bscfa Val from dogs fed pet compositions.

DETAILED DESCRIPTION

Figures 1A, 1B, 1C:
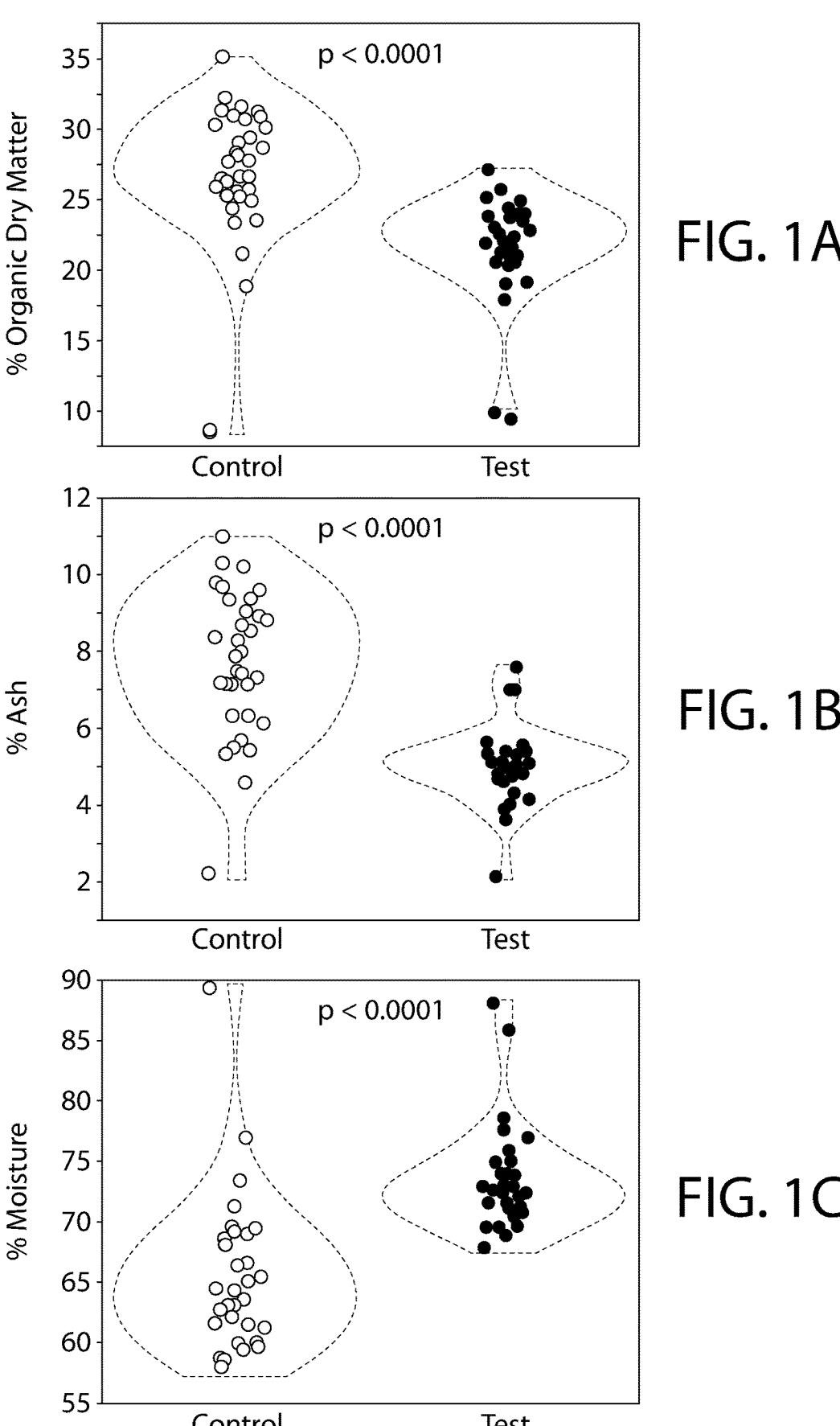
FIGS. 1a-1c depict charts showing result comparisons on stool organic dry matter, ash, and moisture from dogs fed pet compositions.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other applications and methods. It is to be understood that the invention is not limited in its application to the details of any particular embodiment shown. The terminology used herein is for the purpose of description and not to limit the invention, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", "containing", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight of the total composition. Reference to a molecule, or to molecules, being present at a "wt. %" refers to the amount of that molecule, or molecules, present in the composition based on the total weight of the composition.

According to the present application, use of the term "about" in conjunction with a numeral value refers to a value that may be +/−5% of that numeral. As used herein, the term "substantially free" is intended to mean an amount less than about 5.0 weight %, less than 3.0 weight %, 1.0 wt. %; preferably less than about 0.5 wt. %, and more preferably less than about 0.25 wt. % of the composition.

As used herein, the term "effective amount" refers to an amount that is effective to elicit the desired biological response, including the amount of a composition that, when administered to a subject, is sufficient to achieve an effect toward the desired result. The effective amount may vary depending on the composition, the disease, and its severity and the age, weight, etc., of the subject to be treated. The effective amount can include a range of amounts. As is understood in the art, an effective amount may be in one or more doses, i.e., a single dose or multiple doses may be required to achieve the desired endpoint.

As used herein, the term "wt. %" generally refers to the weight percentage based on the total weight of the pet food composition.

Unless defined otherwise, all technical and scientific terms used herein have the same meanings as commonly understood by one of ordinary skill in the art to which this invention belongs. All patents, patent applications, publications, and other references cited or referred to herein are incorporated by reference in their entireties for all purposes. In the event of a conflict in a definition in the present disclosure and that of a cited reference, the present disclosure controls.

The present disclosure is directed toward pet food compositions and methods of using such pet food compositions for the treatment of domestic pets. In certain embodiments, the pet is a dog. In other embodiments, the dog suffers from gastroenteritis.

The present inventors have surprisingly and unexpectedly discovered that providing animals a pet food diet comprising lysine, betaine, and glutamic acid present in a total amount of about 7 wt. % or more, based on the weight of the pet food composition; and one or more fatty acids having an aliphatic chain of 6 to 12 carbons (e.g., C8 fatty acid and/or C10 fatty acid), and omega-3 fatty acid (e.g., omega-3 C18 fatty acid) present in a total amount of about 3.3 wt. % or more, based on the weight of the pet food composition, provides for enhanced health benefit for the animal. For example, the pet food compositions may advantageously contain an amount of protein that is higher than conventional pet food compositions for pets having IBD, without exacerbating or increasing the symptoms of IBD and/or colonic putrefaction. In certain embodiments, glutamine may also be included within the pet food composition. In certain embodiments, the pet food composition may include glutamic acid and/or salts thereof (e.g., monosodium glutamate), glutamine, or a combination of two or more thereof.

Such enhanced health benefit may be exemplified by numerous aspects. In a first aspect, the health benefit may be to increase the dietary protein of the animal without an increase in colonic putrefaction. In another aspect, the health benefit may be to increase beneficial biomarkers. In another aspect, the health benefit may be to beneficially modify the microbiome of an animal. In one aspect, the health benefit may be to increase the lean mass of the animal. In another aspect, the health benefit may be to increase the lean mass of an obese animal. In another aspect, the health benefit may be to increase the lean mass of a dog. The lean mass may be defined as absolute mass or as a lean mass percent of total mass.

In one aspect, the present disclosure therefore provides pet food compositions comprising lysine, betaine, and glutamic acid present in a total amount of about 7 wt. % or more, based on the weight of the pet food composition; and C8 fatty acid, C10 fatty acid, and omega-3 C18 fatty acid present in a total amount of about 3.3 wt. % or more, based on the weight of the pet food composition. In certain embodiments, the composition further comprises flax, citrus pulp, beet pulp, and cranberry pomace. In certain embodiments, the flax, citrus pulp, beet pulp, and cranberry pomace is present in a total amount of about 6% or more, based on the weight of the pet food composition.

The lysine may be present at various amounts or concentrations. The lysine may be included in various forms, such as, but not limited to, a salt, monoprotonated zwitterionic salt, hydrochloride (HCl) salt, peptidyl forms of lysine such as, but not limited to, mono-, di-, tri-, and oligo-peptide forms. In one embodiment, lysine may be present in an amount of from about 0.5% to about 6.3%, based on the weight of the pet food composition. For example, lysine may be present in an amount of about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.0 weight %, about 5.5 weight %, about 6.0 weight %, about 6.3 weight %, or any ranges thereof, based on the total weight of the pet food composition. In another example, lysine may be present in an amount of from about 0.5% to about 6%, about 0.8% to about 5.5%, about 1.0% to about 5.0%, or about 1.5% to about 4%, based on the weight of the pet food composition. In further embodiments, lysine is present in an amount of about 0.5% or more, about 1.5% or more, about 2.5% or more, or about 2.7% or more up to about 6.3%, based on the weight of the pet food composition. In further embodiments, lysine is present in an amount of about 0.5% to 6%, about 1% to about 5%, about 2% to about 4%, or about 2% to about 3%, based on the weight of the pet food composition.

The betaine may be present at various amounts or concentrations. In one embodiment, betaine may be present in an amount of from about 0.2% to about 5%, based on the weight of the pet food composition. For example, betaine may be present in an amount of about 0.2 weight %, about 0.4 weight %, about 0.6 weight %, about 0.8 weight %, about 1.0 weight %, about 1.2 weight %, about 1.4 weight %, about 1.6 weight %, about 1.8 weight %, about 2.0 weight %, about 2.5 weight %, about 3.0 weight %, about 3.5 weight %, about 4.0 weight %, about 4.5 weight %, about 5.0 weight %, or any ranges thereof, based on the total weight of the pet food composition. In another example, betaine may be present in an amount of from about 0.2 wt. % to about 4 wt. %, about 0.3 wt. % to about 4.5 wt. %, about 0.4 wt. % to about 3.0 wt. %, or about 0.5 wt. % to about 2 wt. %, based on the weight of the pet food composition. In further embodiments, betaine is present in an amount of about 0.2 wt. % or more, about 0.4 wt. % or more, about 0.8 wt. % or more, or about 1 wt. % or more up to about 5 wt. %, based on the weight of the pet food composition. In further embodiments, betaine is present in an amount of about 0.2 wt. % to 4 wt. %, about 0.2 wt. % to about 3 wt. %, about 0.2 wt. % to about 2 wt. %, or about 0.2 wt. % to about 1 wt. %, based on the weight of the pet food composition.

The glutamic acid, glutamine, a salt thereof, or combinations thereof may be present at various amounts or concentrations. In certain embodiments, glutamic acid may be present in the form of glutamic acid, glutamine, salts thereof, or combinations of two or more thereof. The glutamic acid and/or glutamine may be included in various forms, such as but not limited to, free base, a salt such as a hydrochloride (HCl) salt, peptidyl forms such as, but not limited to, mono-, di-, tri-, and oligo-peptide forms. In one embodiment, glutamic acid, glutamine, salt(s) thereof, and/or a combination of two or more thereof may be present in an amount of from about 0.5 wt. % to about 6.3 wt. %, based on the weight of the pet food composition. For example, the pet food composition may include glutamic acid, glutamine, a salt thereof, and/or a combination of two or more thereof in an amount from about 0.5 wt. % to about 6.3 wt. %, about 0.5 wt. % to about 6 wt. %, about 0.5 wt. % to about 5 wt. %, about 0.5 wt. % to about 4 wt. %, about 0.5 wt. % to about 3 wt. %, about 0.5 wt. % to about 2 wt. %, about 0.5 wt. % to about 1 wt. %; about 1 wt. % to about 6.3 wt. %, about 1 wt. % to about 6 wt. %, about 1 wt. % to about 5 wt. %, about 1 wt. % to about 4 wt. %, about 1 wt. % to about 3 wt. %, about 1 wt. % to about 2 wt. %; about 2 wt. % to about 6.3 wt. %, about 2 wt. % to about 6 wt. %, about 2 wt. % to about 5 wt. %, about 2 wt. % to about 4 wt. %, about 2 wt. % to about 3 wt. %; about 3 wt. % to about 6.3 wt. %, about 3 wt. % to about 6 wt. %, about 3 wt. % to about 5 wt. %, about 3 wt. % to about 4 wt. %; about 4 wt. % to about 6.3 wt. %, about 4 wt. % to about 6 wt. %, about 4 wt. % to about 5 wt. %; about 5 to about 6.3 wt. %, or about 5 to about 6 wt. %, based on the total weight of the pet food composition.

In at some embodiments, glutamic acid, glutamine, salts thereof, and/or a combination of two or more thereof may be present in an amount of about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.0 weight %, about 5.5 weight %, about 6.0 weight %, about 6.3 weight % or any ranges thereof, based on the total weight of the pet food composition. In another example, glutamic acid and/or glutamine may be present in an amount of from about 0.5 wt. % to about 6 wt. %, about 0.8 wt. % to about 5.5 wt. %, about 1.0 wt. % to about 5.0 wt. %, or about 1.5 wt. % to about 4 wt. %, based on the weight of the pet food composition. In further embodiments, glutamic acid and/or glutamine is present in an amount of about 0.5 wt. % or more, about 1.5 wt. % or more, about 2.5 wt. % or more, or about 2.7 wt. % or more up to about 6.3 wt. %, based on the weight of the pet food composition. In further embodiments, glutamic acid and/or glutamine is present in an amount of about 0.5 wt. % to 6 wt. %, about 1 wt. % to about 5 wt. %, about 2 wt. % to about 4 wt. %, or about 2 wt. % to about 3 wt. %, based on the weight of the pet food composition.

The pet food composition may comprise the lysine, betaine, and glutamic acid at various amounts or concentrations. In certain embodiments, the weight ratio of lysine, betaine, and glutamic acid is from about 5.4:1:7.6 to about 6.5:1:9.1. In certain embodiments the weight ratio of lysine, betaine, and glutamic acid is about 5.4:1:7.6. In certain embodiments, lysine is present from about 2 wt. % to about 3.3 wt. %; betaine is present from about 0.4 wt. % to about 0.6 wt. %; and glutamic acid is present from about 3 wt. % to about 4.6 wt. %, based on the weight of the pet food composition. In certain embodiments, lysine is present at about 2.7 wt. %; betaine is present at about 0.5 wt. %; and glutamic acid is present at about 3.8 wt. %, based on the weight of the pet food composition.

A fatty acid is a carboxylic acid with an aliphatic chain, which is either saturated or unsaturated. In organisms, the aliphatic tail usually contains an even number of carbon atoms, from 4 to 28. For example the fatty acid may have an aliphatic tail from 4 to 28 carbons, 4 to 25 carbons, 4 to 22 carbons, 4 to 20 carbons, 4 to 18 carbons, 4 to 15 carbons, 4 to 12 carbons, 4 to 10 carbons; 6 to 28 carbons, 6 to 25 carbons, 6 to 22 carbons, 6 to 20 carbons, 6 to 18 carbons, 6 to 15 carbons, 6 to 12 carbons, 6 to 10 carbons; 8 to 28 carbons, 8 to 25 carbons, 8 to 22 carbons, 8 to 20 carbons, 8 to 18 carbons, 8 to 15 carbons, 8 to 12 carbons, or 8 to 10 carbons. In at least one embodiment, the fatty acid may have one or more fatty acid having an aliphatic tail of 8 to 10 carbons. The pet food composition may include caproic (hexanoic acid), caprylic (octanoic acid), capric (decanoic acid), lauric (dodecanoic acid), myristic (tetradecanoic acid), palmitic (hexadecanoic acid), stearic (octadecanoic acid), arachidic (eicosanoic acid), behenic (docosanoic acid), or a combination of two or more thereof. In some instances, one or more fatty acid(s) is selected from caproic (hexanoic acid), caprylic (octanoic acid), capric (decanoic acid), lauric (dodecanoic acid), myristic (tetradecanoic acid), and a combination of two or more thereof. In at least one embodiment, the fatty acid(s) is selected from caprylic (octanoic acid), capric (decanoic acid), lauric (dodecanoic acid), myristic (tetradecanoic acid), and a combination of two or more thereof.

Additionally, the pet food composition may include two or more, three or more, or four or more fatty acids. In one embodiment, the pet food composition includes at least one fatty acid having an aliphatic tail of 8 carbons and at least one fatty acid having an aliphatic tail of 10 carbons.

Fatty acids with 8 carbon atoms may be referred to herein as "C8 fatty acid" or "C8." Fatty acids with 10 carbon atoms may be referred to herein as "C10 fatty acid" or "C10." An example of a saturated C8 fatty acid is caprylic acid. The pet food composition may comprise one or more C8 fatty acids. The C8 fatty acid may be present at various amounts or concentrations. In one embodiment, C8 may be present in an amount of from about 0.5% to about 6.3%, based on the weight of the pet food composition. For example, the C8 fatty acid may be present in an amount of about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.0 weight %, about 5.5 weight %, about 6.0 weight %, about 6.3 weight %, or any ranges thereof, based on the total weight of the pet food composition. In another example, the C8 fatty acid may be present in an amount of from about 0.5 wt. % to about 6 wt. %, about 0.8 wt. % to about 5.5 wt. %, about 1.0 wt. % to about 5.0 wt. %, or about 1.5 wt. % to about 4 wt. %, based on the weight of the pet food composition. In further embodiments, the C8 fatty acid is present in an amount of about 0.5 wt. % or more, about 1.5 wt. % or more, about 2.5 wt. % or more, or about 2.7 wt. % or more up to about 6.3 wt. %, based on the weight of the pet food composition. In further embodiments, the C8 fatty acid is present in an amount of about 0.5 wt. % to 6 wt. %, about 1 wt. % to about 5 wt. %, about 1 wt. % to about 4 wt. %, about 1 wt. % to about 3 wt. %, or about 1 wt. % to about 2 wt. %, based on the weight of the pet food composition.

An example of a saturated C10 fatty acid is capric acid. The pet food composition may comprise one or more C10 fatty acids. The C10 fatty acid may be present at various amounts or concentrations. In one embodiment, the C10 fatty acid may be present in an amount of from about 0.5 wt. % to about 6.3 wt. %, based on the weight of the pet food composition. For example, the C10 fatty acid may be present in an amount of about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.0 weight %, about 5.5 weight %, about 6.0 weight %, about 6.3 weight %, or any ranges thereof, based on the total weight of the pet food composition. In another example, the C10 fatty acid may be present in an amount of from about 0.5% to about 6%, about 0.8% to about 5.0%, about 1.0% to about 4.0%, or about 1.0% to about 3%, based on the weight of the pet food composition. In further embodiments, the C10 fatty acid is present in an amount of about 0.5% or more, about 1.5% or more, about 2.5% or more, or about 2.7% or more up to about 6.3%, based on the weight of the pet food composition. In further embodiments, the C10 fatty acid is present in an amount of 0.5% to 6%, about 1% to about 5%, about 1% to about 4%, about 1% to about 3%, or about 1% to about 2%, based on the weight of the pet food composition.

The pet food compositions typically comprise one or more omega-3 fatty acids in an amount that typically ranges from about 0.2% to about 5%, based on the weight of the pet food composition. For example, omega-3 fatty acid may be present in the pet food compounds in an amount of from about 0.2 wt. % to about 5 wt. %, about 0.2 wt. % to about 4 wt. %, about 0.2 wt. % to about 3 wt. %, about 0.2 wt. % to about 2 wt. %; about 0.5 wt. % to about 5 wt. %, about 0.5 wt. % to about 4 wt. %, about 0.5 wt. % to about 3 wt. %, about 0.5 wt. % to about 2 wt. %; about 1 wt. % to about 5 wt. %, about 1 wt. % to about 4 wt. %, about 0.2% to about 3 wt. %, about 0.2% to about 2 wt. %; about 1 wt. % to about 5 wt. %, about 1 wt. % to about 4 wt. %, about 1 wt. % to about 3 wt. %, about 1 wt. % to about 2 wt. %; about 2 wt. % to about 5 wt. %, about 2 wt. % to about 4 wt. %, about 2% to about 3 wt. %; about 3 wt. % to about 5 wt. %, about 3 wt. % to about 4 wt. %; or about 4 wt. % to about 5 wt. %, based on the total weight of the pet food composition. In some embodiment, the omega-3 fatty acids are present in the pet food compositions in an amount from about 0.2 weight %, about 0.4 weight %, about 0.6 weight %, about 0.8 weight %, about 1.0 weight %, about 1.2 weight %, about 1.4 weight %, about 1.6 weight %, about 1.8 weight %, about 2.0 weight %, about 2.5 weight %, about 3.0 weight %, about 3.5 weight %, about 4.0 weight %, about 4.5 weight %, about 5.0 weight %, or ranges thereof, based on the total weight of the pet food composition.

The omega-3 fatty acids may have an aliphatic tail of 16 to 24 carbons, 17 to 24 carbons, 18 to 24 carbons, 19 to 24 carbons, 20 to 24 carbons; 16 to 23 carbons, 17 to 23 carbons, 18 to 23 carbons, 19 to 23 carbons, 20 to 23 carbons; 16 to 22 carbons, 17 to 22 carbons, 18 to 22 carbons, 19 to 22 carbons, or 20 to 22 carbons. Preferably, the pet food composition comprises an omega-3 fatty acid having at least one aliphatic tail of 18 to 22 carbons. The omega-3 fatty acid may comprise linolenic acid, stearidonic acid, eicosatetraenoic acid, eicosapentaenoic acid, docosapentaenoic acid, docosahexaenoic acid, or a combination of two or more thereof.

The omega-3 fatty acid may comprise at least one omega-3 C18 fatty acid. An example of an omega-3 C18 fatty acid is alpha-linolenic acid (ALA). The pet food composition may comprise one or more omega-3 C18 fatty acids. The omega-3 C18 fatty acid may be selected from alpha-linolenic acid, stearidonic acid, and a combination thereof. The omega-3 C18 fatty acid may be present at various amounts or concentrations. In one embodiment, omega-3 C18 fatty acid may be present in an amount of from about 0.2% to about 5%, based on the weight of the pet food composition. For example, omega-3 C18 fatty acid may be present in an amount of about 0.2 weight %, about 0.4 weight %, about 0.6 weight %, about 0.8 weight %, about 1.0 weight %, about 1.2 weight %, about 1.4 weight %, about 1.6 weight %, about 1.8 weight %, about 2.0 weight %, about 2.5 weight %, about 3.0 weight %, about 3.5 weight %, about 4.0 weight %, about 4.5 weight %, about 5.0 weight %, or ranges thereof, based on the total weight of the pet food composition. In another example, omega-3 C18 fatty acid may be present in an amount of from about 0.2% to about 4%, about 0.3% to about 4.5%, about 0.4% to about 3.0%, or about 0.5% to about 2%, based on the weight of the pet food composition. In further embodiments, omega-3 C18 fatty acid is present in an amount of about 0.2% or more, about 0.4% or more, about 0.8% or more, or about 1% or more up to about 5%, based on the weight of the pet food composition. In further embodiments, omega-3 C18 fatty acid is present in an amount of about 0.2% to 4%, about 0.2% to about 3%, about 0.2% to about 2%, or about 0.2% to about 1%, based on the weight of the pet food composition.

The pet food composition may comprise the C8 fatty acid, C10 fatty acid, and omega-3 C18 fatty acid at various amounts or concentrations. In certain embodiments, wherein the weight ratio of C8 fatty acid, C10 fatty acid, and omega-3 C18 fatty acid is from about 2.21:1.86:1 to about 2.65:2.23:9.1. In further embodiments, the weight ratio of C8 fatty acid, C10 fatty acid, and omega-3 C18 fatty acid is from about 2:1.3:1 to about 4.5:3.5:1 or about 2:1.3:1 to about 4:3:1. In yet further embodiments, the weight ratio of C8 fatty acid, C10 fatty acid, and omega-3 C18 fatty acid is from about 1.75:1.1:1 to about 2.21:1.86:1. In certain embodiments, the weight ratio of C8 fatty acid, C10 fatty acid, and omega-3 C18 fatty acid is about 2.21:1.86:1. In certain embodiments, the C8 fatty acid is present from about 1.15 wt. % to about 1.73 wt. %; the C10 fatty acid is present from about 0.97 wt. % to about 1.45 wt. %; and the omega-3 C18 fatty acid is present from about 0.52 wt. % to about 0.78 wt. %, based on the weight of the pet food composition. In certain embodiments, the C8 fatty acid is present at about 1.44 wt. %; the C10 fatty acid is about 1.21 wt. %; and the omega-3 C18 fatty acid is present at about 0.65 wt. %, based on the weight of the pet food composition.

The protein of the composition may be present at various amounts or concentrations. In one embodiment, the protein may be present in an amount of from about 20 wt. % to about 45 wt. %, based on the weight of the pet food composition. For example, the protein may be present in an amount of about 20 weight %, about 25 weight %, about 30 weight %, about 35 weight %, about 40 weight %, about 45 weight %, or a range thereof, based on the total weight of the pet food composition. In another example, the protein may be present in an amount of from about 25 wt. % to about 40 wt. %, from about 30 wt. % to about 40 wt. %, or about 30 wt. % to about 35 wt. %, based on the weight of the pet food composition. In certain embodiments, the protein is present in an amount of about 20 wt. % to about 35 wt. %, about 25 wt. % to about 35 wt. %, or about 28 wt. % to about 35 wt. %, based on the weight of the pet food composition.

The total dietary fiber of the composition may be present at various amounts or concentrations. In one embodiment, total dietary fiber may be present in an amount of less than 20%, based on the weight of the pet food composition. In certain embodiments, the total dietary fiber is present in an amount of about 10 wt. % to about 20 wt. %, based on the weight of the pet food composition. For example, total dietary fiber may be present in an amount of about 10.0 weight %, about 10.5 weight %, about 11.0 weight %, about 11.5 weight %, about 12.0 weight %, about 12.5 weight %, about 13.0 weight %, about 13.5 weight %, about 14.0 weight %, about 14.5 weight %, about 15.0 weight %, about 15.5 weight %, about 16.0 weight %, about 16.5 weight %, about 17.0 weight %, about 17.5 weight %, about 18.0 weight %, about 18.5 weight %, about 19.0 weight %, about 19.5 weight %, about 20.0 weight %, or a range thereof, based on the total weight of the pet food composition. In another example, total dietary fiber may be present in an amount of from about 10 wt. % to about 18 wt. %, about 12 wt. % to about 18 wt. %, or about 15 wt. % to about 18 wt. %, based on the weight of the pet food composition. In further embodiments, total dietary fiber is present in an amount of about 15 wt. % to about 20 wt. %, about 16 wt. % to about 19 wt. %, or about 16 wt. % to about 18 wt. %, based on the weight of the pet food composition.

The moisture of the composition may be present at various amounts or concentrations. The moisture may be present at various amounts or concentrations. In one embodiment, the moisture may be present in an amount of from about 5 wt. % to about 15 wt. %, based on the weight of the pet food composition. For example, the moisture may be present in an amount of about 5.0 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, about 10.0 weight %, about 10.5 weight %, about 11.0 weight %, about 11.5 weight %, about 12.0 weight %, about 12.5 weight %, about 13.0 weight %, about 13.5 weight %, about 14.0 weight %, about 14.5 weight %, about 15.0 weight %, or a range thereof, based on the total weight of the pet food composition. In another example, the moisture may be present in an amount of from about 8 wt. % to about 13 wt. %, about 9 wt. % to about 13 wt. %, about 9 wt. % to about 11 wt. %, or about 9 wt. % to about 13 wt. %, based on the weight of the pet food composition. In certain embodiments, the moisture is present in an amount of about 10 wt. % to about 12 wt. %, about 10.5 wt. % to about 12 wt. %, or about 10.5 wt. % to about 11.5 wt. %, based on the weight of the pet food composition.

The compositions of the present invention may optionally comprise additional ingredients suitable for use in pet food compositions. Examples of such ingredients include, but are not limited to, fat, carbohydrates, dietary fibers, amino acids, minerals, trace elements, vitamins, additives.

Carbohydrates can be supplied by any of a variety of sources known by those skilled in the art, including oat fiber, cellulose, peanut hulls, beet pulp, parboiled rice, corn starch, corn gluten meal, and any combination of those sources. Grains supplying carbohydrates can include, but are not limited to, wheat, corn, barley, and rice. Carbohydrates content of foods can be determined by any number of methods known by those of skill in the art. Generally, carbohydrate percentage can be calculated as nitrogen free extract ("NFE"), which can be calculated as follows: NFE=100%-moisture %-protein %-fat %-ash %-crude fiber %.

Dietary fiber refers to components of a plant which are resistant to digestion by an animal's digestive enzymes. Dietary fiber includes soluble and insoluble fibers. Soluble fibers are resistant to digestion and absorption in the small intestine and undergo complete or partial fermentation in the large intestine, e.g., beet pulp, guar gum, chicory root, *psyllium*, pectin, blueberry, cranberry, squash, apples, oats, beans, citrus, barley, fructooligosaccharides (FOS), or peas. Insoluble fibers can be supplied by any of a variety of sources, including, for example, cellulose, whole wheat products, wheat oat, corn bran, flax seed, grapes, celery, green beans, cauliflower, potato skins, fruit skins, vegetable skins, peanut hulls, rye berries, sweet potato, and soy fiber. Crude fiber includes indigestible components contained in cell walls and cell contents of plants such as grains, for example, hulls of grains such as rice, corn, and beans. Typical fiber amounts in compositions of the present disclosure can be from about 0 to 10%, or about 1% to about 5%. For instance, the amount of fiber (e.g., crude fiber or dietary fiber) in the pet food composition may be from about 0.1 to about 10% by weight, about 0.1 to about 9% by weight, about 0.1 to about 8% by weight, about 0.1 to about 7% by weight, about 0.1 to about 6% by weight, about 0.1 to about 5% by weight, about 0.1 to about 4% by weight, about 0.1 to about 3% by weight, about 0.1 to about 2% by weight, about 0.1 to about 1% by weight; about 0.5 to about 10% by weight, about 0.5 to about 9% by weight, about 0.5 to about 8% by weight, about 0.5 to about 7% by weight, about 0.5 to about 6% by weight, about 0.5 to about 5% by weight, about 0.5 to about 4% by weight, about 0.5 to about 3% by weight, about 0.5 to about 2% by weight, about 0.5 to about 1% by weight; about 1 to about 10% by weight, about 1 to about 9% by weight, about 1 to about 8% by weight, about 1 to about 7% by weight, about 1 to about 6% by weight, about 1 to about 5% by weight, about 1 to about 4% by weight, about 1 to about 3% by weight, about 1 to about 2% by weight; about 1.5 to about 10% by weight, about 1.5 to about 9% by weight, about 1.5 to about 8% by weight, about 1.5 to about 7% by weight, about 1.5 to about 6% by weight, about 1.5 to about 5% by weight, about 1.5 to about 4% by weight, or about 1.5 to about 3% by weight, based on the total weight of the pet food composition.

Amino acids, including essential amino acids, can be added to the compositions of the present disclosure as free amino acids, or supplied by any number of sources, e.g., crude protein, to the compositions of the present disclosure. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine. In addition, taurine, while technically not an amino acid but a derivative of cysteine, is an essential nutrient for cats.

The compositions of the present invention may optionally comprise fat. The term "fat" generally refers to a lipid or mixture of lipids that may generally be a solid or a liquid at ordinary room temperatures (e.g., 25° C.) and pressures (e.g., 1 atm). In some instances, the fat may be a viscous liquid or an amorphous solid at standard room temperature and pressure. Fat can be supplied by any of a variety of sources known by those skilled in the art, including meat, meat by-products, canola oil, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The compositions of the present disclosure may contain at least about 9 wt. % (or from about 9 wt. % to about 25 wt. %, or from about 10 wt. % to about 20 wt. %, or from about 10 wt. % to about 15 wt. %) total fat, based on the total weight of the pet food composition. In some cases, the fat in the compositions is crude fat. Crude fat may be included into the compositions in amounts of from about 10 to about 20 weight %, about 10 to about 18 weight %, about 10 to about 16 weight %; about 12 to about 20 weight %, about 12 to about 18 weight %, or about 12 to about 16 weight %, based on the total weight of the composition. In some cases, it may be preferable that about 50 weight % or more, about 60 weight % or more, about 70 weight % or more, about 80 weight % or more, or about 90 weight % or more of the total fat is obtained from an animal source. Alternatively, about 50 weight % or more, about 60 weight % or more, about 70 weight % or more, about 80 weight % or more, or about 90 weight % or more of the total fat may be obtained from a plant source.

The pet food composition, in some cases, may include ash. The amount of ash preset in the food composition may be from about 1 to about 15% by weight, about 1 to about 13% by weight, about 1 to about 11% by weight, about 1 to about 10% by weight, about 1 to about 9% by weight, about 1 to about 8% by weight, about 1 to about 7% by weight, about 1 to about 6% by weight, about 1 to about 5% by weight, about 1 to about 4% by weight, about 1 to about 3% by weight; about 3 to about 15% by weight, about 3 to about 13% by weight, about 3 to about 11% by weight, about 3 to about 10% by weight, about 3 to about 9% by weight, about 3 to about 8% by weight, about 3 to about 7% by weight, about 3 to about 6% by weight, about 3 to about 5% by weight; about 4 to about 15% by weight, about 4 to about 13% by weight, about 4 to about 11% by weight, about 4 to about 10% by weight, about 4 to about 9% by weight, about 4 to about 8% by weight, about 4 to about 7% by weight; about 5 to about 15% by weight, about 5 to about 13% by weight, about 5 to about 11% by weight, about 5 to about 10% by weight, about 5 to about 9% by weight, about 5 to about 8% by weight, about 5 to about 7% by weight, based on the weight of the pet food composition.

The pet food compositions of the present disclosure can also contain one or more minerals and/or trace elements, e.g., calcium, phosphorus, sodium, potassium, magnesium, manganese, copper, zinc, chromium, molybdenum, selenium, or iron salts having counterions such as, for example chloride, iodide, fluoride, sulfide or oxide, in amounts required to avoid deficiency and maintain health. These amounts are known by those of skill in the art, for example, as provided in the Official Publication of the Associate of American Feed Control Officials, Inc. ("AAFCO"), Nutrient Requirements of Dogs and Cats, 2006. Typical mineral amounts are about 0.1 wt. % to about 4 wt. % or about 1 wt. % to about 2 wt. %, based on the total weight of the pet food compositions.

The pet food compositions of the present invention can also include vitamins in amounts required to avoid deficiency and maintain health. These amounts and methods of measurement are known by those skilled in the art. For example, the Official Publication of the Associate of American Feed Control Officials, Inc. ("AAFCO"), Nutrient Requirements of Dogs and Cats, 2006 provides recommended amounts of such ingredients for dogs and cats. As contemplated herein, vitamins can include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, choline, inositol, niacin, and pantothenic acid. Typical vitamin amounts in the composition of the invention are about from 0 to about 3% or about 1% to about 2%.

The compositions of the present disclosure can additionally comprise other additives such as palatability enhancers and stabilizers in amounts and combinations familiar to one of skill in the art. Stabilizing substances include, for example, substances that tend to increase the shelf life of the composition. Other examples of other such additives potentially suitable for inclusion in the compositions of the invention include, for example, preservatives, colorants, antioxidants, flavorants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches. The concentration of such additives in the composition typically can be up to about 5% by weight, based on the total weight of the pet food composition. In some embodiments, the concentration of such additives (particularly where such additives are primarily nutritional balancing agents, such as vitamins and minerals) is from about 0% to about 2.0% by weight, based on the total weight of the pet food composition. In some embodiments, the concentration of such additives (again, particularly where such additives are primarily nutritional balancing agents) is from about 0% to about 1.0% by weight, based on the total weight of the pet food composition.

In certain preferred embodiments, the pet food composition comprises flax, citrus pulp, beet pulp, and cranberry pomace. The pet food composition may comprise flax, citrus pulp, beet pulp, and cranberry pomace at various amounts and concentrations. In certain embodiments, the flax, citrus pulp, beet pulp, and cranberry pomace is present in a total amount of about 6 wt. % or more, based on the weight of the pet food composition. In other embodiments, the weight ratio of flax, citrus pulp, beet pulp, and cranberry pomace is from about 2:1.5:1.5:1 to about 2.4:1.8:1.8:1. In further embodiments, the weight ratio of flax, citrus pulp, beet pulp, and cranberry pomace is from about 2:1.5:1.5:1. In certain embodiments, flax is present from about 1.6 wt. % to about 2.4 wt. %; citrus pulp is present from about 1.2 wt. % to about 1.8 wt. %; beet pulp is present from about 1.2 wt. % to about 1.8 wt. %, and cranberry pomace is present from about 0.8 wt. % to about 1.2 wt. %, based on the weight of the pet food composition. In further embodiments, flax is present at about 2 wt. %; citrus pulp is present at about 1.5 wt. %; beet pulp is present at about 1.5 wt. %, and cranberry pomace is present at about 1.0 wt. %, based on the weight of the pet food composition.

Foods of any consistency or moisture content are contemplated, e.g., the compositions of the present invention can be, for example, a dry, moist or semi-moist animal food composition. In some embodiments, the moisture content is from about 3 wt. % to about 90 wt. % of the total weight of the composition. "Semi-moist" refers to a food composition containing from about 25 wt. % to about 35 wt. % moisture, based on the total weight of the pet food composition. "Moist" food refers to a food composition that has a moisture content of about 60 wt. % to 90 wt. % or greater, based on the total weight of the pet food composition. "Dry" food refers to a food composition with about 3 wt. % to about 12 wt. % moisture content, based on the total weight of the pet food composition, and is often manufactured in the form of small bits or kibbles.

In certain aspects, the present application further discloses a method of making any of the compositions of the present disclosure. In preparing a composition of the present invention in wet or canned form, any ingredient (e.g., soluble fiber and desired ratio of linolenic acid):(total 18 carbon polyunsaturated fatty acids) generally can, for example, be incorporated into the composition during the processing of the formulation, such as during and/or after mixing of other components of the composition. Distribution of these components into the composition can be accomplished by conventional means. In some embodiments, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients can be mixed in a vessel suitable for heating while blending the components. Heating of the mixture can be effected using any suitable manner, such as, for example, by direct steam injection or by using a vessel fitted with a heat exchanger. Following the addition of the last ingredient, the mixture can be heated to a temperature range of from about 50° F. (10° C.) to about 212° F. (100° C.). In some instances, the mixture can be heated to a temperature range of from about 70° F. (21° C.) to about 140° F. (60° C.). Temperatures outside these ranges are generally acceptable but may be commercially impractical without use of other processing aids. When heated to the appropriate temperature, the material will typically be in the form of a thick liquid. The thick liquid can be filled into cans. When filled into cans, a lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Pet food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, then forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

In another aspect, the present disclosure provides for a method for treating, preventing, or ameliorating gut microbiome putrefaction in a companion animal, comprising feeding an effective amount of a composition as described herein. The companion animal may be a dog or cat.

In some embodiments, the present disclosure provides for a pet food composition for mitigating gut microbiome putrefaction, comprising; lysine, betaine, and glutamic acid present in a total amount of about 7 wt. % or more, based on the weight of the pet food composition; C8 fatty acid, C10 fatty acid, and omega-3 C18 fatty acid present in a total amount of about 3.3 wt. % or more, based on the weight of the pet food composition; and flax, citrus pulp, beet pulp, and cranberry pomace present in a total amount of about 6 wt. % or more, based on the weight of the pet food composition.

In certain embodiments, the present disclosure provides for a method for mitigating gut microbiome putrefaction in a companion animal, comprising feeding an effective amount of any of the compositions described above.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The study used both healthy dogs and dogs diagnosed with, or suspected of having, chronic gastroenteritis. Dog feed was provided twice a day. Dogs underwent a prefeed period where they were fed control composition for 1 week. Next, dogs were randomly separated into either a control or testing group and fed the respective food composition for 4 weeks. A cross feed period was then implemented by switching food composition for each group such that the control group was fed the test composition and the testing group was now fed the control composition. The cross feed period was maintained for 4 weeks. Blood and feces samples were collected throughout the feeding periods.

TABLE 1

| Food Compositions (wt. %) | | |
| --- | --- | --- |
| | Control | Test |
| Chicken liver and heart | 28.3 | 25 |
| Potato | 56.4 | 40 |
| Milk protein (glutamine source) | 0 | 6 |
| Cellulose | 4 | 3 |
| Lysine | 0 | 1 |
| Betaine | 0 | 0.5 |
| Flax | 0 | 2 |
| Citrus pulp | 0 | 1.5 |
| Beet pulp | 0 | 1.5 |
| Cranberry pomace | 0 | 1 |
| Animal fat and soybean oil | 4.7 | 2 |
| Medium chain triglyceride (C8 and C10 fatty acid source) | 0 | 3 |
| Glutamine concentrate (glutamine source) | 0 | 1 |
| Vitamins, minerals and amino acids | 4.7 | 5.3 |
| Palatant | 0 | 2 |
| Processing aids | 1.9 | 2.2 |

TABLE 2

| Feed Analytical Results | | |
| --- | --- | --- |
| | Control (Predicted) | Test |
| % Moisture | 8 | 9.9 |
| % Fat | 13.9 | 14.3 |
| % Protein | 18.5 | 26.3 |
| % Ash | 5.3 | 5.7 |
| % Crude Fiber | 2.9 | 2.9 |
| Betaine | 0 | 0.5 |
| Glutamine/Glutamate | 2.4 | 3.8 |
| Lysine | 1.5 | 2.7 |
| C8 Fatty acid | 0 | 1.7 |
| C10 Fatty Acid | 0 | 1.3 |
| Omega-3 C18 fatty acid | 0.4 | 0.6 |

Example 2

Results from the studies. Fresh feces were assessed for subjective quality parameters according to a 5-point index, where 1 does not have solid form and 5 is >80% firm. Table 3 shows the mean, SE and t-test statistical comparison of the stool quality after dogs were fed either the test or the control composition. The inventive test food stool scores are significantly higher than the control food.

TABLE 3

| Stool quality | | | |
| --- | --- | --- | --- |
| Diet | Mean | Standard Error | P value for difference |
| Control | 4.15 | 0.08 | 0.028 |
| Test | 4.45 | 0.11 | |

Table 4 shows the food intake from the control and test compositions. It is readily apparent that the test food composition is just as palatable as the state of the art food, or control composition. There was no detrimental impact observed on palatability.

TABLE 4

| Food Intake from Compositions | | | |
| --- | --- | --- | --- |
| Diet | Mean | Standard error | P value for difference |
| Control | 93.0 | 1.8 | Not significant |
| Test | 93.9 | 1.8 | |

Table 5 shows biomarker results from dogs fed the food compositions.

TABLE 5

| Biomarker Results from dogs fed pet food compositions. | | |
| --- | --- | --- |
| | Control | Test |
| $Log_{10}$[Fecal IgA] | 0.441 | 0.829 |
| Albumin (g/dL) | 3.36 | 3.44 |
| Total protein (g/dL) | 5.63 | 5.74 |
| HCT (%) | 46.35 | 48.49 |
| Red blood cells (M/μL) | 6.84 | 7.16 |
| Hemoglobin (g/dL) | 15.98 | 16.68 |
| IRF (%) | 17.69 | 15.37 |
| $Log_{10}$[eosinophils %] | 0.61 | 0.51 |

As shown in Table 5, dogs fed the test composition showed enhanced health benefits, as evidenced by biomarker analysis. Fecal IgA is a marker of gut health, having a direct proportional relationship to the gut health. With respect to this biomarker, the increased IgA resulting from the test composition is representative of a healthier gut state. Albumin and protein T are representative of circulating protein status. With respect to these biomarkers, it is seen that the test composition improves circulating protein.

FIG. 1 shows that stool derived from animals consuming the test composition showed higher moisture levels. Furthermore, stools from the dogs fed the test food were subjectively gauged as having a stool score that indicates increased firmness by analysts blinded to diet identity when compared to stool derived from animals consuming the control composition (Table 3). These results show that the stool resulting from the test food composition produced firmer stool. Taken together, the test composition produced higher moisture and firmer stool.

Figure 2A:
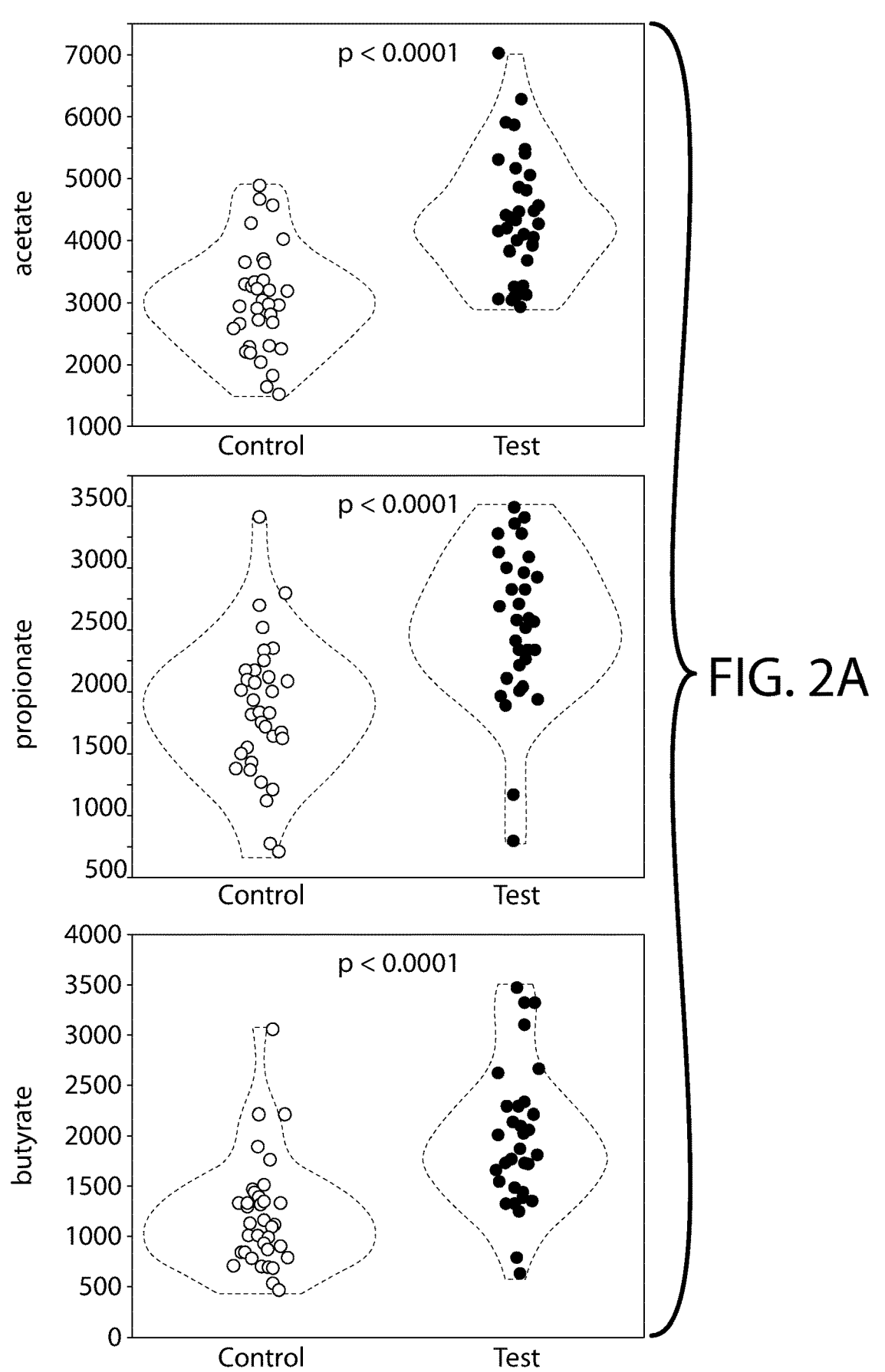
FIGS. 2a-2c depict charts showing the result comparison on fecal short chain fatty acids acetate, propionate, and butyrate from dogs fed pet food compositions.
Figure 2B:
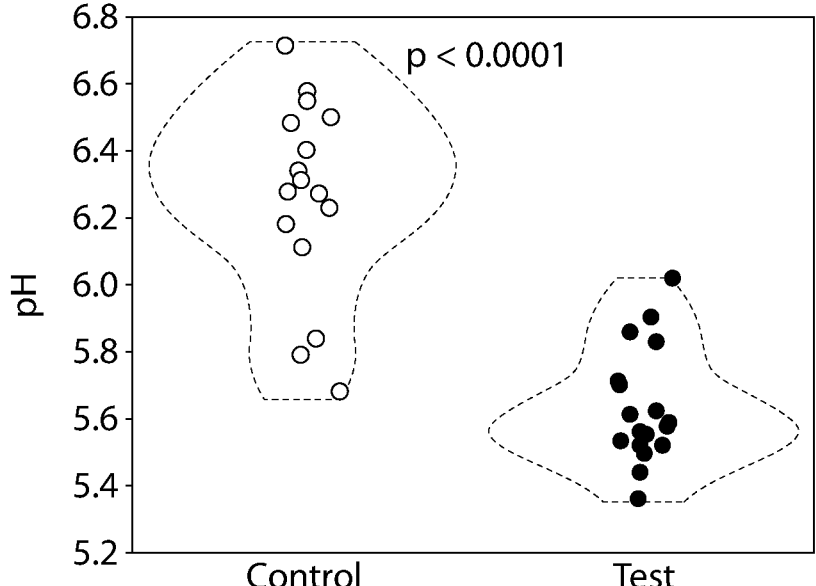
Figure 2C:
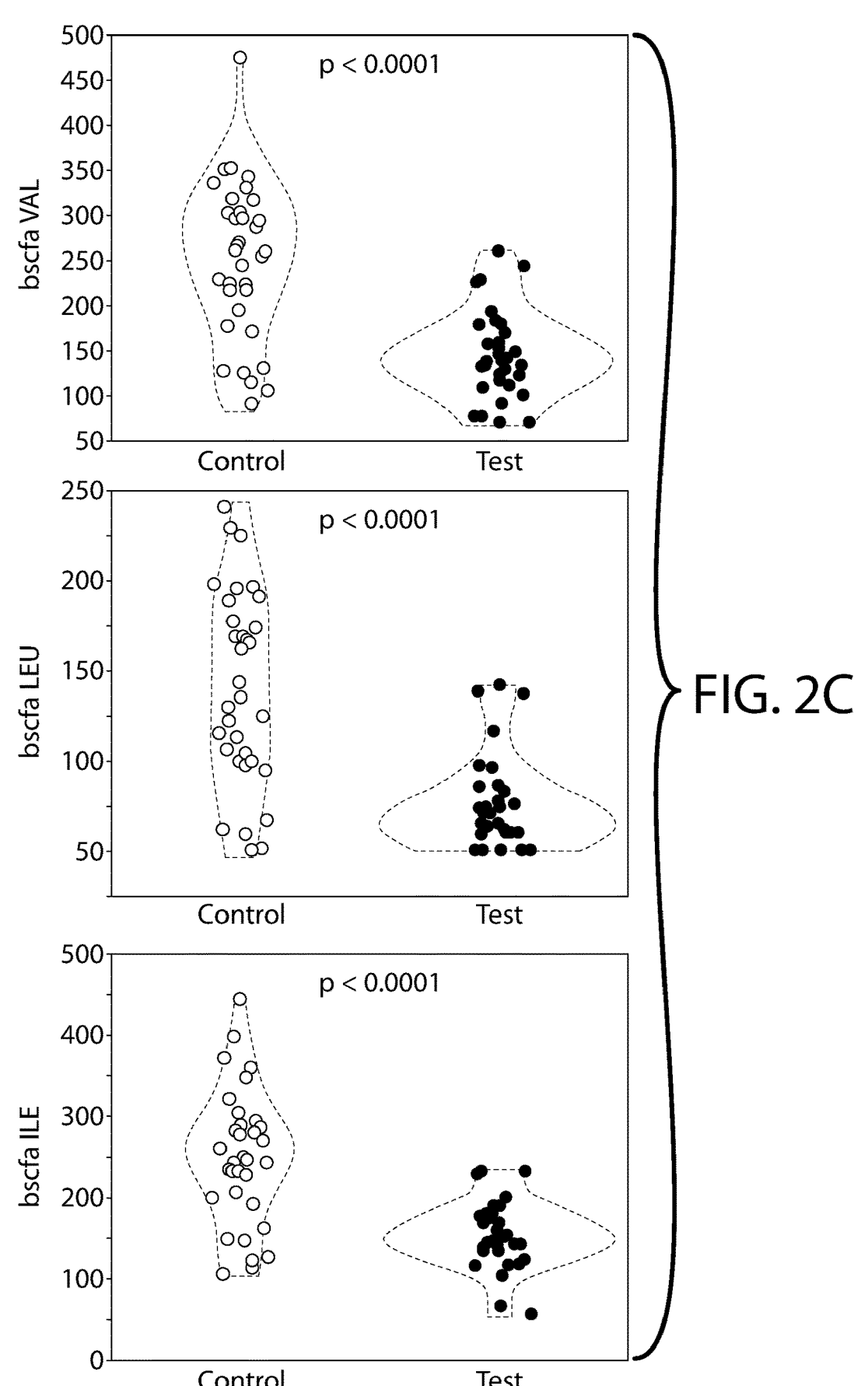

FIG. 2a shows that the test composition increases saccharolysis, as represented by increased presence of short chain fatty acids (SCFA's) acetate, propionate and butyrate. All three SCFA's were increased by at least 30%, when compared to the control composition. FIG. 2b shows that the test composition lowers, or improves, colonic pH. FIG. 2c shows that the test composition lowers all three tested bSCFA's, which result is associated with decreased putrefaction. The decrease was at least 30% when compared to control composition.

Figure 3:
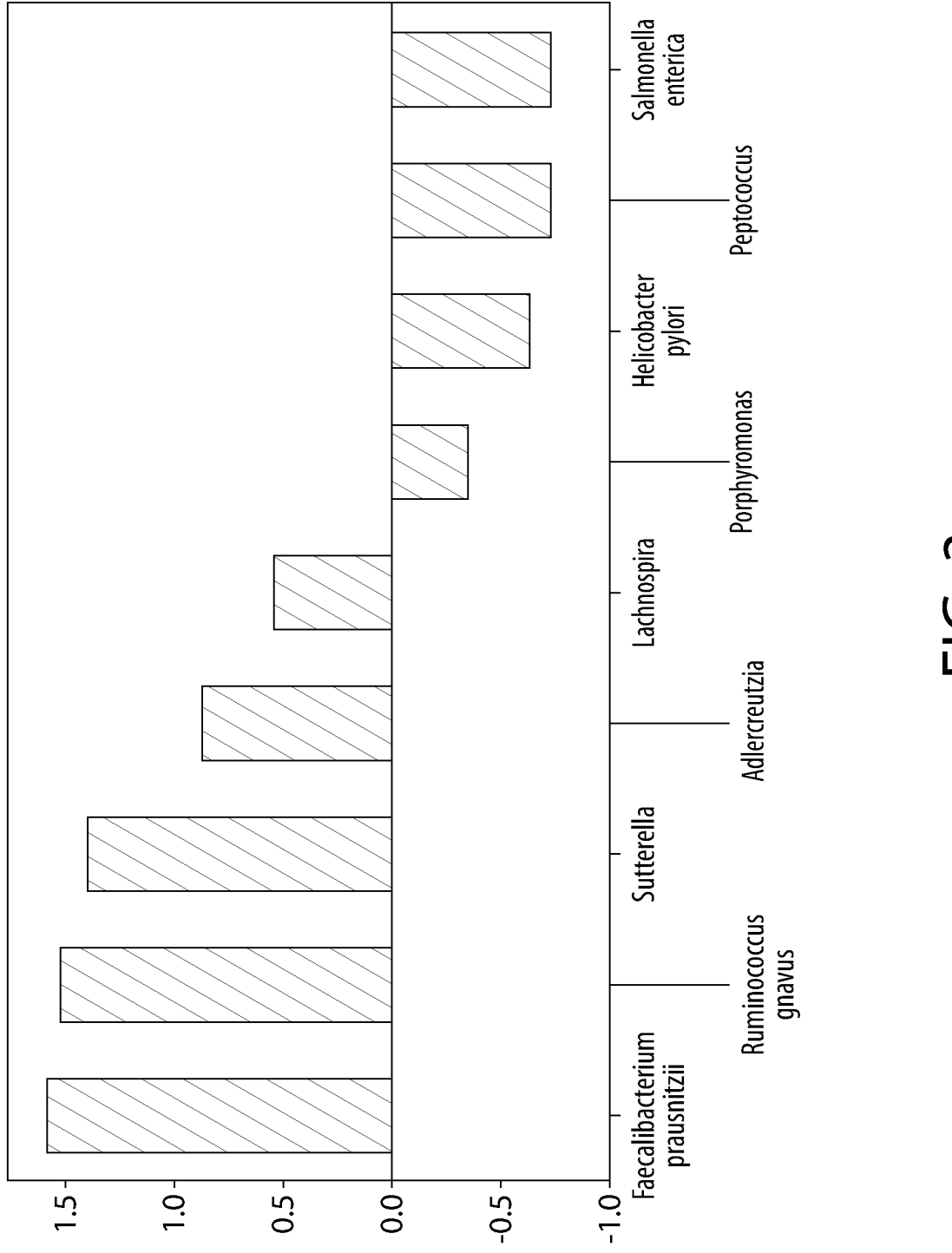
FIG. 3 depicts a chart showing the effects on the gut microbiome from dogs fed pet food compositions.

FIG. 3 shows that the test composition increases beneficial gut microbes, which ferments fiber to short chain fatty acids, while concurrently decreasing potential pathobionts and proteolytic microbes. Specifically, microbes classified as *faecalibacterium* prausnitii, ruminococcus gnavus, genus *sutterella*, genus *adlercreutzia*, and genus *lachnospira* showed increased levels while genus *porphyromonas*, *helicobacter* s *pylori*, genus *peptococcus*, and *Salmonella enterica* showed decreased levels.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. A pet food composition for mitigating gut microbiome putrefaction, comprising:

an amino acid component comprising lysine, betaine, and glutamic acid, wherein lysine is present from 2 wt. % to 3.3 wt. %; the betaine is present from 0.4 wt. % to 0.6 wt. %; and the glutamic acid is present from 3 wt. % to 4.6 wt. %, based on the total weight of the pet food composition;

a fatty acid component comprising: a C8 fatty acid present from 0.5 wt. % to 6.3 wt. %; a C10 fatty acid present from 0.5 wt. % to 6.3 wt. %; and an omega-3 C18 fatty acid present from 0.2 wt. % to 5 wt. %, based on the total weight of the pet food composition; and a fiber component comprising: a fiber source selected from: flax seed; citrus pulp; beet pulp; cranberry pomace; or a combination thereof, present in an amount of 0.1 wt % to 10 wt %, based on the total weight of the pet food composition, wherein the weight ratio of lysine:betaine:glutamic acid is from about 5.4:1:7.6 to about 6.5:1:9.1.

2. The pet food composition according to claim 1, wherein the weight ratio of C8 fatty acid:C10 fatty acid:omega-3 C18 fatty acid is from about 2.21:1.86:1 to about 2.65:2.23:1.

3. The pet food composition according to claim 1, comprising:

from about 1.15 wt. % to about 1.73 wt. % of a C8 fatty acid;

from about 0.97 wt. % to about 1.45 wt. % of a C10 fatty acid; and from about 0.52 wt. % to about 0.78 wt. % of an omega-3 C18 fatty acid.

4. The pet food composition of claim 1, wherein the omega-3 fatty acid is selected from linolenic acid, stearidonic acid, eicosatetraenoic acid, eicosapentaenoic acid, docosapentaenoic acid, docosahexaenoic acid, or a combination thereof.

5. The pet food composition of claim 1, further comprising caproic acid, caprylic acid, capric acid, lauric acid, or a combination.

6. The pet food composition according to claim 1, wherein the amino acid component comprises:

about 2.7 wt. % of lysine;

about 0.5 wt. % of betaine; and about 3.8 wt. % of glutamic acid.

7. The pet food composition according to claim 1, wherein the fiber component comprises flax seed, beet pulp, and cranberry pomace, and wherein the weight ratio of flax seed:citrus pulp:beet pulp:cranberry pomace is from about 2:1.5:1.5:1 to about 2.4:1.8:1.8:1 or about 2:1.5:1.5:1.

8. The pet food composition of claim 1, wherein the fiber component comprises:

from about 1.6 wt. % to about 2.4 wt. % of flax seed;

from about 1.2 wt. % to about 1.8 wt. % of citrus pulp;

from about 1.2 wt. % to about 1.8 wt. % of beet pulp; and from about 0.8 wt. % to about 1.2 wt. % of cranberry pomace.

9. A method for treating or ameliorating a symptom associated with gut microbiome putrefaction in a companion animal or mitigating gut microbiome putrefaction, the method comprising feeding an effective amount of the pet food composition of claim 1 to the companion animal in need thereof.

10. The method according to claim 9, wherein the companion animal is a dog.

\* \* \* \* \*